(12) United States Patent
Altobelli

(10) Patent No.: US 8,157,774 B1
(45) Date of Patent: Apr. 17, 2012

(54) APPARATUS FOR STEM CELL COLLECTION AND METHODS THEREOF

(75) Inventor: David E. Altobelli, Hollis, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 315 days.

(21) Appl. No.: 11/687,149

(22) Filed: Mar. 16, 2007

Related U.S. Application Data

(60) Provisional application No. 60/782,755, filed on Mar. 16, 2006.

(51) Int. Cl.
*A61M 1/00* (2006.01)

(52) U.S. Cl. .......................... 604/317; 604/319; 600/573

(58) Field of Classification Search .................. 604/317, 604/319, 321; 600/573, 580, 584
See application file for complete search history.

(56) References Cited

U.S. PATENT DOCUMENTS

| | | |
|---|---|---|
| 4,572,181 A | 2/1986 | Mattler |
| 5,053,025 A | 10/1991 | Knippscheer |
| 5,059,168 A | 10/1991 | Stone |
| 5,190,556 A | 3/1993 | Hessel |
| 5,199,441 A * | 4/1993 | Hogle ........................... 600/566 |
| 5,342,328 A | 8/1994 | Grossman et al. |
| 5,356,373 A | 10/1994 | Dracker |
| 5,415,665 A | 5/1995 | Hessel et al. |
| 5,520,699 A | 5/1996 | Hessel et al. |
| 5,575,795 A | 11/1996 | Anderson |
| 5,575,796 A | 11/1996 | King et al. |
| 5,690,646 A | 11/1997 | Gruenberg |
| 5,860,989 A | 1/1999 | Webb |
| 5,879,318 A | 3/1999 | Van Der Heiden et al. |
| 5,919,176 A * | 7/1999 | Kuypers et al. ............... 604/317 |
| 5,919,702 A | 7/1999 | Purchio et al. |
| 5,993,429 A | 11/1999 | Kuypers et al. |
| 6,179,819 B1 | 1/2001 | Haswell |
| 6,190,368 B1 | 2/2001 | Kuypers et al. |
| 6,302,854 B1 * | 10/2001 | Paderni ......................... 600/573 |
| 6,440,110 B2 | 8/2002 | Kuypers et al. |
| 6,443,958 B1 | 9/2002 | Watson, Jr. et al. |
| 6,461,645 B1 | 10/2002 | Boyse et al. |
| 6,491,682 B2 | 12/2002 | Paderni |
| 6,638,282 B2 | 10/2003 | Ramsey et al. |
| D481,793 S | 11/2003 | Rao et al. |
| 7,131,958 B2 | 11/2006 | Deverre |
| 7,311,905 B2 | 12/2007 | Hariri |
| 2002/0132343 A1 | 9/2002 | Lum |
| 2002/0183679 A1 * | 12/2002 | Deverre ....................... 604/6.15 |
| 2003/0180269 A1 | 9/2003 | Hariri |
| 2006/0020227 A1 * | 1/2006 | Moore et al. .................. 600/573 |

FOREIGN PATENT DOCUMENTS

| | | |
|---|---|---|
| JP | 10136978 | 10/1998 |
| WO | WO91/09521 | 7/1991 |

OTHER PUBLICATIONS

Bertolini, F., Lazzari, I., Lauri, E., Corsini, C., Castelli, C., Gorini, F., Sirchia, G., Comparative Study of Different Procedures for the Collection and Banking of Umbilical Cord Blood. Journal of Hematotherapy, 4:29-36 (1995).
Will, A. M., Umbilical Cord Blood Transplantation. Archives of Disease in Childhood 1999:80: Jan. 3-6.
Umbilical Cord Matrix, a Rich New Stem Cell Source, theHDlighthouse, Jan. 17, 2003, http://hdlighthouse.org/research/tissue/updates/0030WhartonsJelly.phtml.
Mitchell, K.E., Weiss, M.L., Mitchell, B.M., Martin, P., Davis, D., Morales, L., Helwig, B., Beerenstrauch, M., Abou-Easa, K., Hhildreth, T., Troyer, D., Matrix Cells from Wharton's Jelly Form Neurons and Glia. Stem Cells 21:50-60 (2003).
Kas,, J., Breakthrough Isolating Embryo-Quality Stem Cells From Blood. Institute of Physics, Jun. 19, 2005, http://www.sciencedaily.com/print.php?url=/releases/2005/06/050619115816,htm.
New Technique Boosts Potential for Growing Stem Cells, University of Toronto, May 2, 2002, http://www.sciencedaily.com/releases/2002/05/020529072452.htm.
Cairo, M.S. and Wagner, J.E., Placental and/or Umbilical Cord Blood: An Alternative Source of Hematopoietic Stem Cells for Transplantation. Blood, vol. 90 No. 12 (Dec. 15), 1997: pp. 4665-4678.

* cited by examiner

*Primary Examiner* — Maria Leavitt
(74) *Attorney, Agent, or Firm* — Michelle Saquet Temple

(57) ABSTRACT

Apparatus and methods for collecting stem cells from an umbilical cord utilize a plurality of needles that are inserted into the umbilical cord. The needles may be fenestrated, and may have a common output to a line via which the stem cells are collected. A negative pressure source, such as a vacuum, may be used to draw the cells through the needles and the line. Apparatus for holding the umbilical cord, compressing the umbilical cord, positioning the plurality of needles in relation to the umbilical cord, guiding insertion of the needles toward and into the umbilical cord, withdrawing blood from the umbilical cord, and/or collecting blood withdrawn from the umbilical cord may be provided. One or more one-way check valves may be used to control fluid flow. Additionally or alternatively, a shunt may be used during blood collection to prevent backflow through the needles.

15 Claims, 15 Drawing Sheets

APPARATUS FOR STEM CELL COLLECTION AND METHODS THEREOF

CROSS-REFERENCE TO RELATED APPLICATION

This application claims priority from U.S. Patent Application No. 60/782,755 entitled STEM CELL COLLECTION AND ADMINISTRATION filed on Mar. 16, 2006 in the name of David E. Altobelli, which is hereby incorporated by reference in its entirety.

FIELD OF THE INVENTION

Various embodiments of this invention relate to devices and methods for collecting stem cells from tissues and for delivering stem cells to a patient.

BACKGROUND

The current process in the delivery of babies requires the umbilical cord to be clamped and cut shortly after a child is born. The function of the cord is the transmission of nutrients, oxygen and carbon dioxide between mother and baby through blood flowing in the cord. The cord, which extends from the placenta, is thus engorged with fetal blood at birth.

It has become known that the blood present in the umbilical cord at birth has considerable potential curative value, e.g. for extraction of neutral stem cells with potential transplant value and for use in bone marrow transplants for treatment of cancer and immunodeficiency disorders. In the past, umbilical cord blood has been discarded with the placenta. However, commercial services are now available for collection and storage of umbilical cord blood for personal or family use.

Common practices to obtain this blood include the draining of the cord segment directly into an open vial and direct extraction from the cord by syringe or needle. The draining method requires one person to hold an open ended sample vial below the cord opening while a second person opens a metal clamp and attempts to direct the blood flow into the opening. In this open system, the cord segment must be hand squeezed towards the vial, likely causing many contaminants to flow into the vial including possibly the mother's vaginal blood, amniotic fluids and Wharton's gel. In addition, when a syringe or needle is used to extract the blood directly from the cord in an open or closed system, care must be taken to prevent inadvertent needle sticks. In addition, single syringes may be limited in the amount of blood that they are able to extract.

SUMMARY OF THE INVENTION

In a first embodiment of the invention, there is a method for collecting stem cells from an umbilical cord. A fluid collection device having a plurality of needles is used to withdraw stem cells from the umbilical cord by inserting the plurality of needles into the umbilical cord and collecting the stem cells. The needles may be fenestrated, and may have a common output to a line via which the stem cells are collected. A negative pressure source, such as a vacuum, may be used to draw the cells through the needles and the line.

An embodiment of the invention features a device for collecting fluid from an umbilical cord that includes a positioning means for positioning a plurality of needles in relation to a held umbilical cord, a guide means for guiding the insertion of the plurality of needles toward and into the umbilical cord, and a collection means for withdrawing blood from the umbilical cord. The device may include a means for holding the umbilical cord in a fixed position. The device may include a source of negative pressure.

In another exemplary embodiment of the invention, there is a device for collecting fluid, such as blood, from an umbilical cord. The device includes a needle carrier, which holds an array of needles, a holder with a cavity for holding an umbilical cord in place during insertion of the needles, and a handle for applying force to the needle carrier. The holder has a guide for guiding the needle carrier toward the umbilical cord.

The cavity may be formed from an upper portion hinged to a backstop. The backstop is advantageously composed of a material that is puncture resistant. The cavity in the holder may have a height that is less than the diameter of the cord, and may have a rough interior structure to assist in flattening and holding the umbilical cord in place. When force is applied to the handle, the needle carrier travels and inserts the needles into the umbilical cord. The carrier may be mounted slidably with respect to the cavity so that application of force to the handle causes of the needle carrier to slide in the guide, thereby causing insertion of the needles in the cord. The needles may be fenestrated.

The plurality of the needles may have an output into a common conduit, through which fluid may pass from the needles to a collection vessel, such as a collection bag. An anticoagulant may be provided in the collection bag to prevent clotting of collected blood. The conduit may be integral to the carrier. A source of negative pressure, or suction, may be connected to the conduit from the umbilical cord to the collection vessel. One or more check valves may be included to enforce the one-way flow of fluid.

In embodiments of the invention, a sealable bag may be used to encase a placenta attached to the umbilical cord. The bag may have a port for attaching a source of suction, such as a pump for a syringe. Application of suction will cause a pressure differential between the inside and outside of the bag, thereby urging additional blood to flow from the placenta, through the umbilical cord, and into the collection device.

In yet another embodiment of the invention, there is a method for delivering cells to a patient. The method includes providing a source of frozen cells and cell-delivery fluid for delivering cells. Cell-delivery fluid is transported to a warming device, which warms the cell-delivery fluid. The so-warmed fluid is transported to frozen cells, thereby causing thawing of at least some of the cells and mixing of at least some of the cells with the cell-delivery fluid. The so-thawed cells are then transported to the patient. The fluid used for this method may be a fluid that is derived from the blood of the patient, such as the patient's own blood or plasma. The fluid may be an IV fluid such as saline or Ringer's solution. The delivery fluid may also be a mixture of an IV fluid and a fluid derived from the blood of the patient.

BRIEF DESCRIPTION OF THE DRAWINGS

The foregoing features of the invention will be more readily understood by reference to the following detailed description, taken with reference to the accompanying drawings, in which.

It should be noted that the foregoing figures and the elements depicted therein are not necessarily drawn to consistent scale or to any scale. Unless the context otherwise suggests, like elements are indicated by like numerals.

DETAILED DESCRIPTION

Definitions. As used in this description and the accompanying claims, the following terms shall have the meanings indicated, unless the context otherwise requires:

A "Needle" shall mean any slender instrument suitable for the siphoning of blood or other biological material.

An "IV fluid" shall mean any fluid compatible with cells and suitable for delivering intravenously to a patient. Examples of IV fluids include normal saline and lactated Ringer's solution.

Embodiments of the device and method include a procedure for obtaining umbilical cord blood and a procedure for improved administration of umbilical cord stem cells to a patient. In various embodiments, a closed collection system may be used that can reduce the risks of microbial and maternal cell contamination during the collection of umbilical cord blood.

Figure 1:
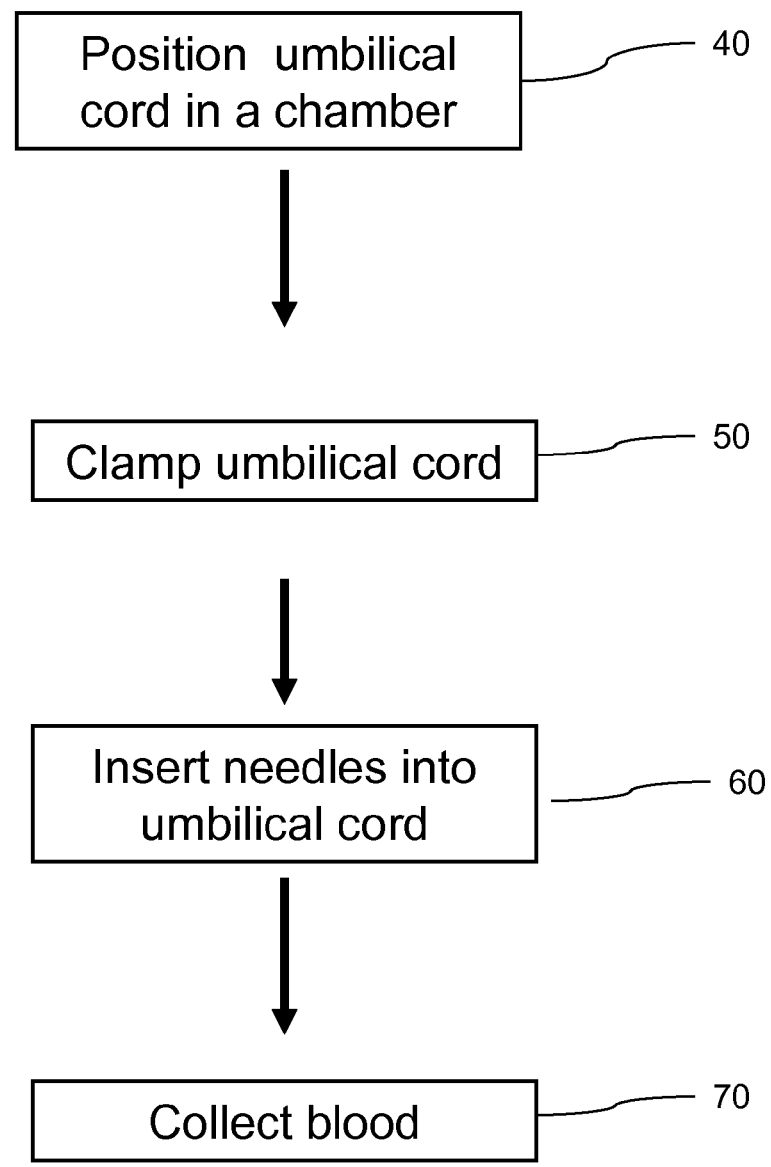
FIG. 1 shows a flow chart for a method of collecting blood from an umbilical cord in accordance with an exemplary embodiment of the present invention.

FIG. 1 shows a flow chart of an embodiment that is a method for efficiently collecting umbilical cord blood for recovery of stem cells or other uses. An umbilical cord blood collection device is provided, examples of which are provided below. The device typically has a chamber for holding an umbilical cord and needles for penetrating the umbilical cord and allowing fluid communication between the blood vessels of the umbilical cord and a collection receptacle. The umbilical cord is positioned in the chamber (step 40), clamped in the chamber (step 50) so as to render it substantially immobile while needles are inserted into the umbilical cord (step 60) to allow blood to be collected (step 70). Collection receptacle and collection bag are used interchangeably throughout. The term collection receptacle includes, but is not limited to, a collection bag.

Figure 2:
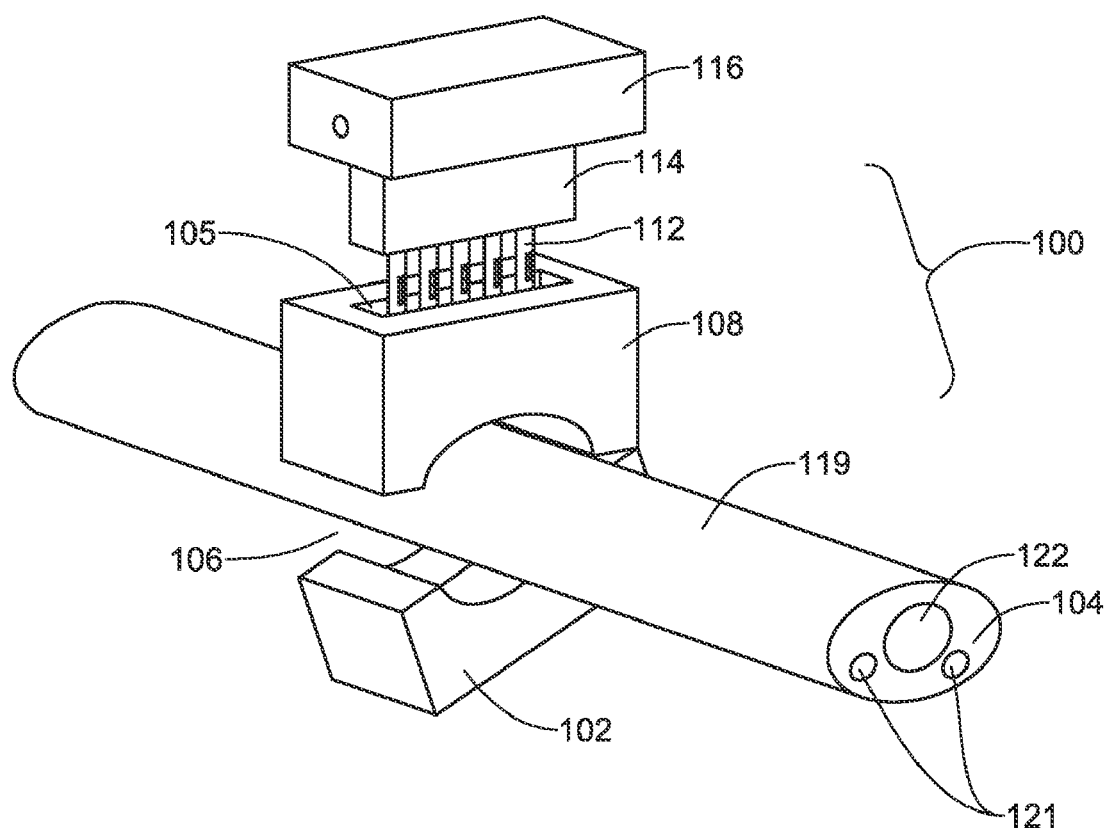
FIG. 2 shows a perspective view of a device for collecting stem cells in an open position in accordance with an exemplary embodiment of the present invention.

With reference to FIG. 2, an umbilical cord blood collection device 100 is shown in a ready-to-use state in accordance with an embodiment of the present invention. The operation of the device 100 includes the steps of positioning the umbilical cord 104 between an upper portion 108 hinged to a backstop 102, closing the upper portion 108 on the backstop 102 to clamp the cord 104 in a chamber 106, inserting one or more needles 112 into the chamber 106 and into the cord 104, and collecting blood from the arteries 121 and the vein 122.

All or a portion of the interior surface of the chamber 106 may include ridges or other surface irregularities to aid in securing the cord 104 through contact with the cord's outer surface 119. The chamber 106 may have a height less than the diameter of a typical umbilical cord 104 so as to flatten the cord and force the arteries 121 and the vein 122 into a side-by-side arrangement to facilitate access by one or more needles 112. Backstop 102 is optionally formed of a hard, needle-penetration-resistant material, such as a suitable plastic. A plurality of needles are typically provided in a substantially parallel arrangement on a needle carrier 114 with a handle 116. A guide slot 105 serves to orient the needle carrier so that by applying force to the handle 116, a user will cause the needles 112 to travel into the chamber 106 and insert into the portion of umbilical cord 104 held in the chamber 106, thereby establishing fluid communication between the sources of blood in the cord 104 and the lumina (not shown) of the needles 112. The handle 116 may engage the upper portion to limit the range of travel of the needle carrier 114 in the slot 105 and prevent the needles from crashing into the backstop 102.

In some embodiments, the umbilical cord blood collection device 100 may be used immediately after birth. In these embodiments, the device may be conveniently located in the surgery room, adjacent to the area of birth, for ready availability. Where there are multiple births, two or more devices may be available in a delivery room. In some embodiments, the umbilical cord blood collection device 100 may be used immediately upon severing the umbilical cord 104. In these embodiments, upon cutting of the umbilical cord by conventional methods, a segment of umbilical cord 104 may be placed in chamber 106.

In some embodiments, the entire blood collection device 100 may be discarded once blood is collected, allowing a user to utilize the umbilical cord blood collection device 100 without ever being exposed to the sharp ends on the needles 112, thus reducing the risk to the user of being injured by the needles. However, in other embodiments, the device can be sterilized in between uses and the needles 112 may be replaced.

In some embodiments, the needles 112 may be fenestrated needles, which in some instances, can allow for greater collection efficiency while reducing the chance of blockage. An umbilical cord 104 typically has three blood vessels: two arteries 121 and one vein 122, and the plurality of needles 112 can increase the probability of drawing blood from more than one of these blood vessels.

The needle carrier 114 may contain at as few as one and as many as about 100 or more needles 112. In certain embodiments, needles 112 may be between about 13 to 30 gauge.

In one embodiment, the needles 112 are preformed into the needle carrier 114 and structured so that the user is not exposed to the sharp ends of the needles 112, the user being protected from the sharp ends by upper portion 108. A tab on the needle carrier 114 may prevent a user from withdrawing the needle carrier 114 from the upper portion 108. The needle carrier 114 has a handle 116 to allow a user to push the needles 112 through the umbilical cord walls 119 when the upper portion 108 and the backstop 102 are in a closed position.

Figure 3:
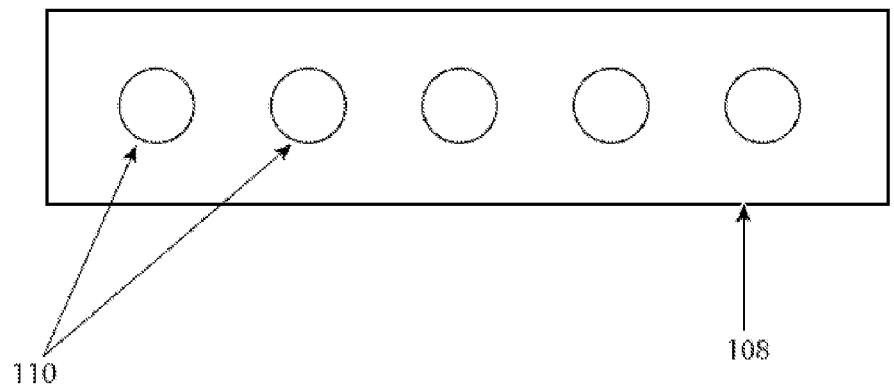
FIG. 3 shows a top view of a portion of a device for collecting stem cells in accordance with an exemplary embodiment of the present invention.

In alternate embodiments a user may prepare to extract blood from the umbilical cord 104 by attaching needles 112 to a needle carrier 114. As seen in FIG. 3, the upper portion 108 may include receiving holes 110 for receiving needles (not shown, shown as 112 in FIG. 4). The needles extend from the needle carrier 114 and are inserted into the receiving holes 110 by a user. In some embodiments, the needles 112 are disposable needles. Disposable needles allows for the option of the device 100 to be reused with simple sterilization of the umbilical cord blood collection device (not shown, shown in FIG. 1 as 100) and insertion of new needles. Sterilization of the container can be accomplished by many techniques known in the art, including but not limited to: exposure to electromagnetic radiation, irradiation with beta particles, and autoclaving of suitable materials in a steam sterilizer.

Figure 4:
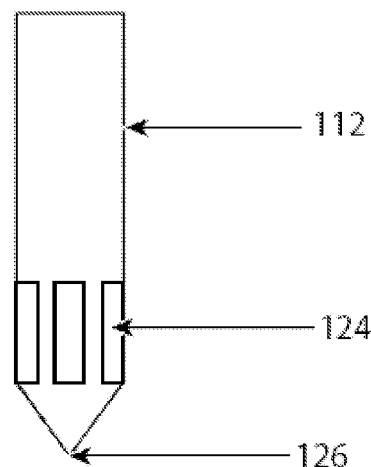
FIG. 4 shows a front view of a fenestrated needle in accordance with an exemplary embodiment of the present invention.

As seen in FIG. 4, one embodiment of the needles 112 is shown. In this embodiment, the needle 112 is a fenestrated needle. However, in other embodiments, any needle may be used. The needles 112 are pointed to help the needle head 126 penetrate the umbilical cord wall. Fenestrations 124 may be provided on the needles 112. Blood can be collected from the arteries 121 and the vein 122 of the umbilical cord 104 through the needle head 126 and through fenestrations 124. In some instances, the fenestrations 124 provide an increased probability of creating a fluidic path between the blood-vessels of the umbilical cord and the lumen of a needle 112 even if the tip of needles is buried in non-blood-vessel tissue.

In some embodiments of the umbilical cord blood collection device (shown in FIG. 1 as 100) the device is entirely or partially disposable and constructed partially or entirely of injection molded plastic components that may be sterilized for a user. However, in other embodiments, the device may be made from stainless steel or any other material having the necessary characteristics for the desired functionality. In other embodiments, the device is partially or entirely non-disposable. The non-disposable parts being sterilized between uses. The device may be sterilized upon manufacturing and placed in a sealed, sterile packaging. A disposable device may also be fabricated from biocompatible metal, other plastics or ceramic materials. Thus, the device can either be entirely or partially disposable. In one embodiment, the entire device is reusable save for the needles. However, in some embodiments, the needles can be reused.

Figure 5:
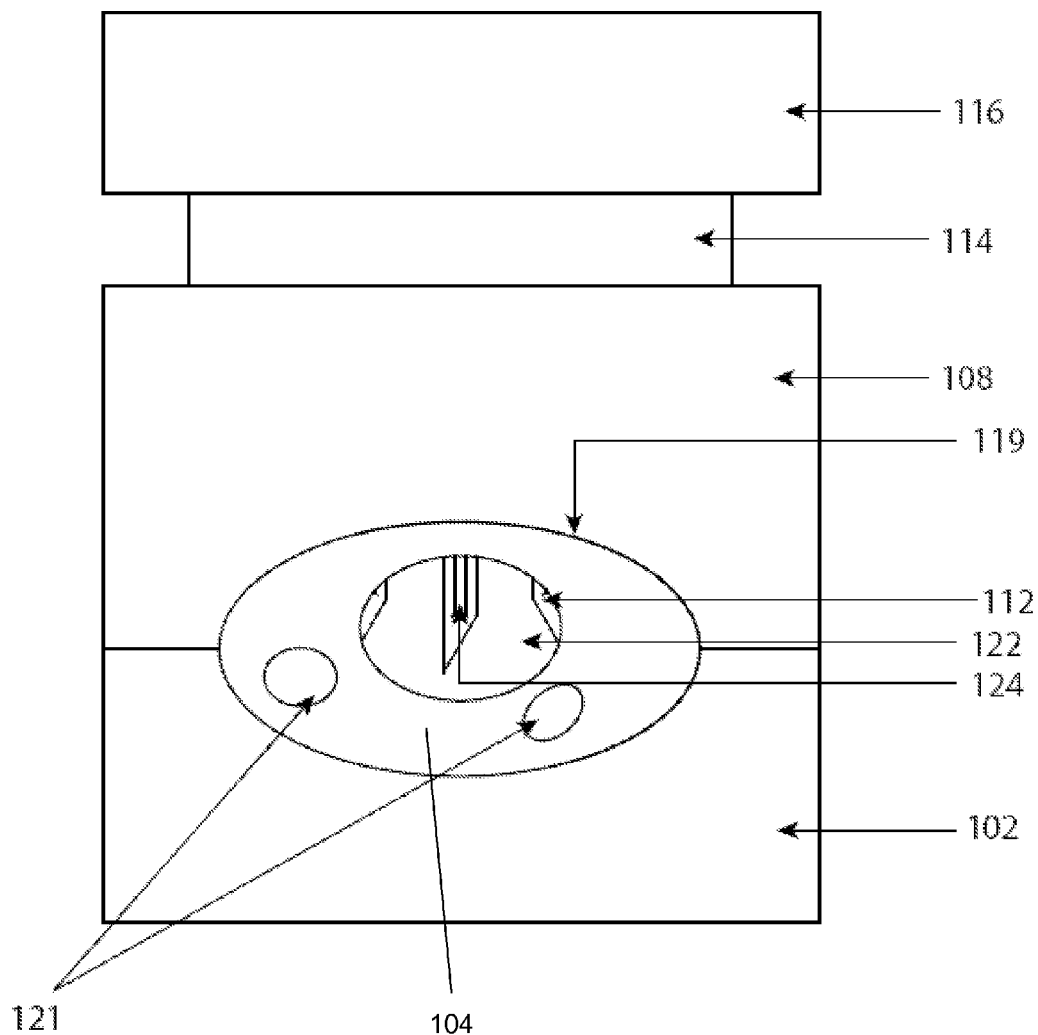
FIG. 5 shows a front view of a device for collecting stem cells in a partially closed position in accordance with an exemplary embodiment of the present invention.

FIG. 5 shows a side view of one embodiment of the device after it has been partially engaged so that the needles 112 are in the process of being pushed downward, toward the arteries 121 and the vein 122. The umbilical cord 104, the arteries 121 and the vein 122 can be seen in cross section. One of the needles 112 can be seen with its tip and fenestrations 124 inserted into the vein 122.

Figure 6:
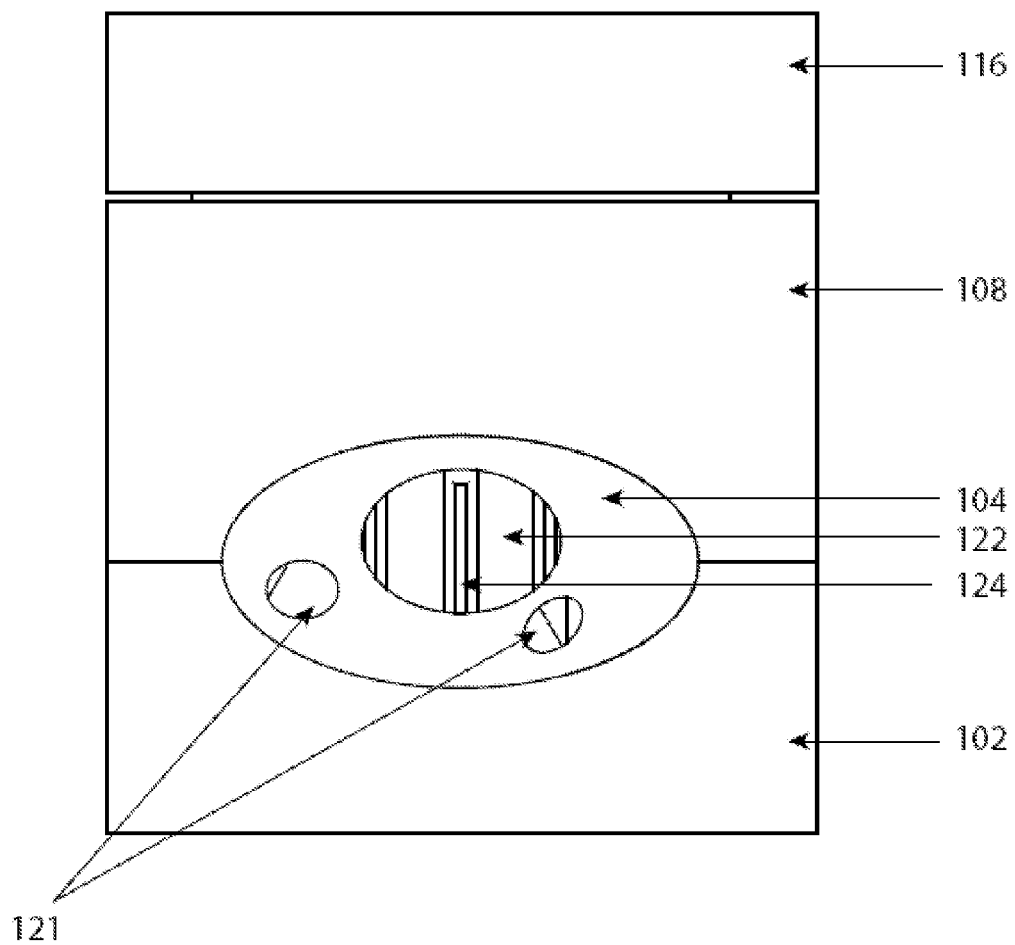
FIG. 6 shows a front view of a device for collecting stem cells in a closed position in accordance with an exemplary embodiment of the present invention.

FIG. 6 shows one embodiment of the device after it has been fully engaged, so that the needles have fully inserted into the umbilical cord 104 and have begun to collect blood from the arteries 121 and the vein 122. Several of the needles are seen to have penetrated through the vein 122, yet at least one fenestration 124 remains within the lumen of the vein even though the tip may be buried in the underlying tissue. Another of the needles is seen to be positioned with its tip within one of the arteries 121. Thus, by having multiple openings at the tips 126 and fenestrations 124, a greater probability of creating a fluidic path between the vein 124 and the downstream collection apparatus is realized. After insertion of the needles, blood is typically collected from the device 100, typically by use of force such as gravity, suction or pressure.

Figure 7:
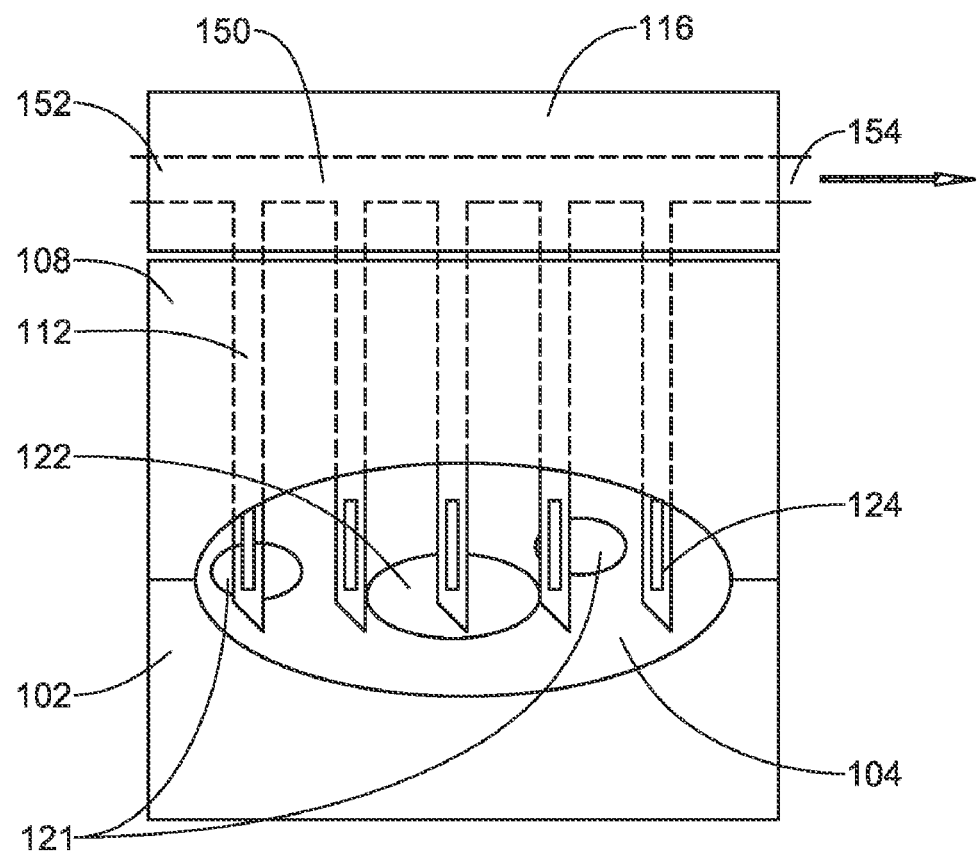
FIG. 7 shows a front view of a device for collecting stem cells having a conduit in accordance with an exemplary embodiment of the present invention.

FIG. 7 shows an embodiment of a device having a conduit 150 within the handle 116. The needles 112 have a first end and a second end wherein the second end is coupled to a common conduit shared by the needles 112. The conduit 150 serves as an exit passageway for the collection of blood and may include an outlet 154 for the blood to exit. In some embodiments, an inlet 152 may be included.

Figure 8:
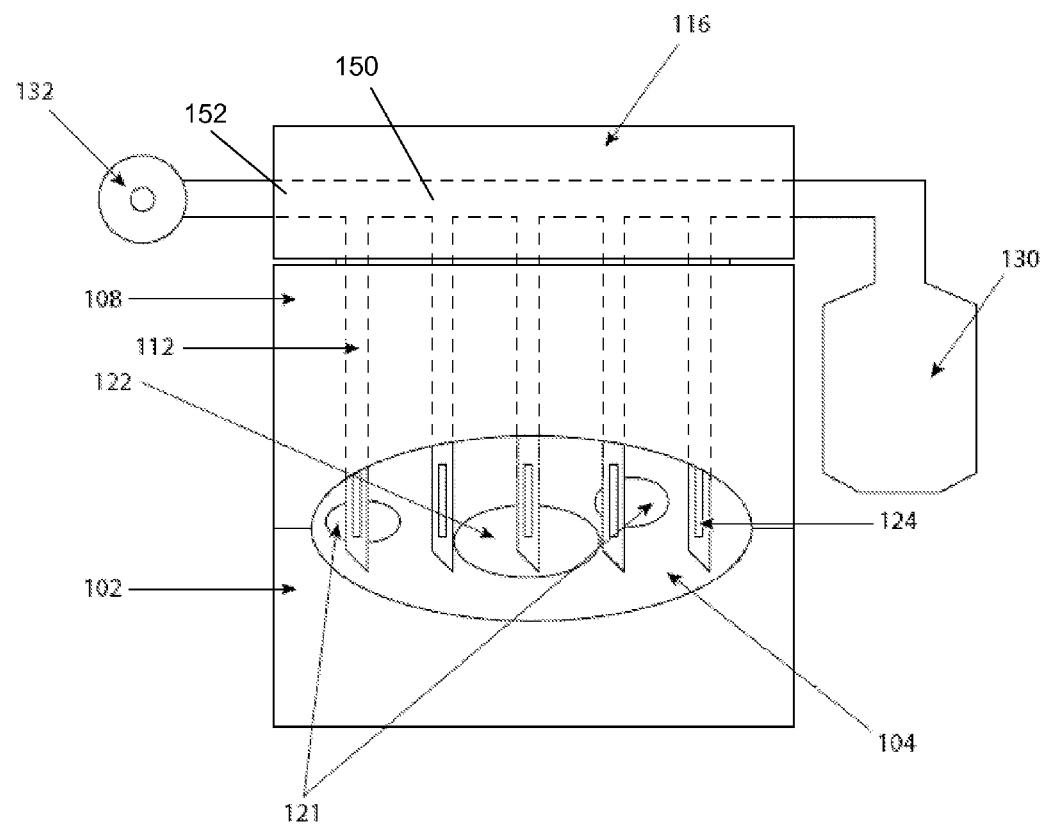
FIG. 8 shows a front view of a device for collecting stem cells having a conduit, a suction source and a collection bag positioned at an outlet of the conduit, in accordance with an exemplary embodiment of the present invention.

FIG. 8 shows one embodiment of a blood collection unit employing suction. A suction source 132 serves to create a pressure differential which induces blood to flow from the arteries 121 and the vein 122 of the umbilical cord 104 via the needles 112 into a conduit 150 and to a collection receptacle 130. The suction source 132 in one embodiment, may be an intermittent wall-type suction source commonly found in the hospital setting. However, in other embodiments, the suction source 132 can be a syringe or any other suitable source, many of which are known to those of skill in the art. For example, manually or automatically withdrawing the plunger of a syringe attached to the inlet 152 will create a suitable suction. The collection receptacle 130 may be held in a position lower than the conduit 150 so as to employ gravity to cause blood to collect in the bag 130. The collection receptacle 130 can be made from any material capable of safely storing the blood. In some embodiment, the collection receptacle 130 is any collection container, including, but not limited to, a bag.

Figure 14:
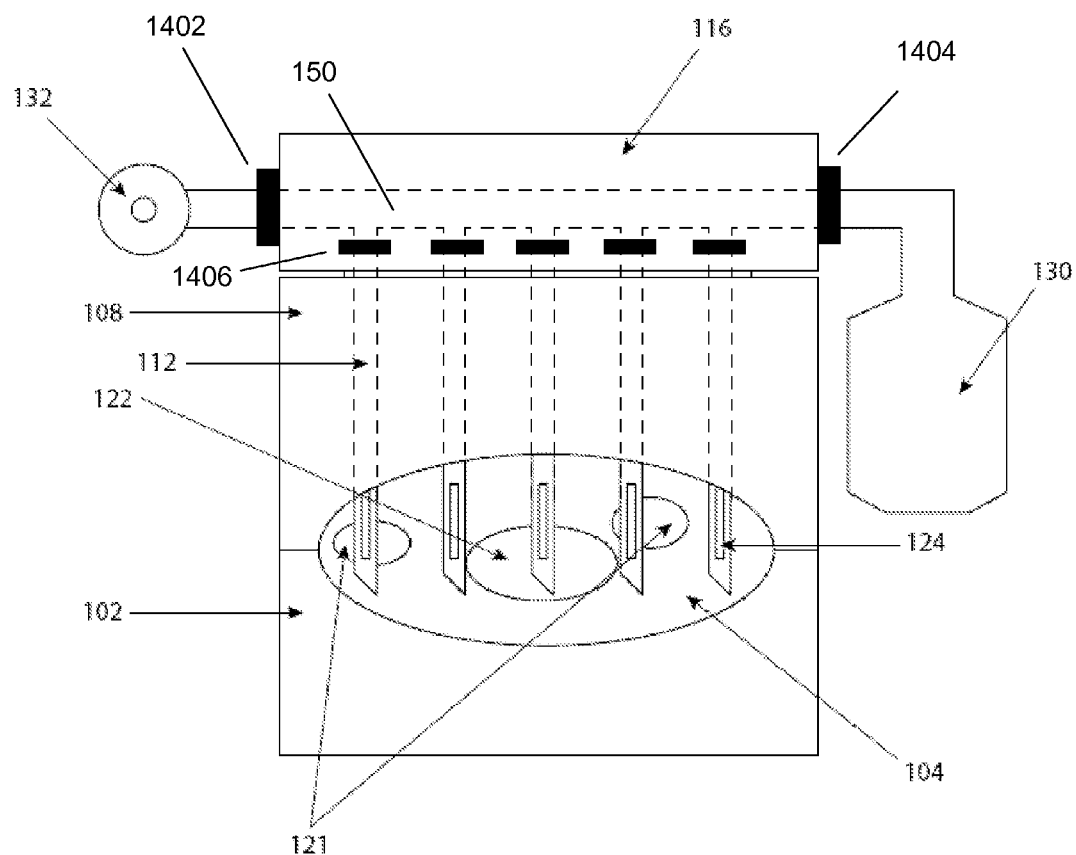
FIG. 14 shows a front view of a device including one or more on-way check valves for controlling fluid flow, in accordance with exemplary embodiments of the present invention.

In some embodiments, one or more one-way check valves may be used to control fluid flow while fluid is being drawn from the umbilical cord 104 and/or while fluid is being collected in the bag 130. For example, as shown in FIG. 14, a one-way check valve 1402 may be employed between the conduit 150 and the suction source 132, e.g., to prevent fluid from being drawn into the source 132. In some embodiments, check valves 1406 may additionally or alternatively be employed above the needles 112, e.g., to prevent fluid from flowing through the needles back into the umbilical cord. In yet further embodiments, a check valve 1404 may additionally or alternatively be employed between the conduit 150 and the collection receptacle 130, e.g., to prevent fluid from being drawn from the receptacle 130.

Figure 15:
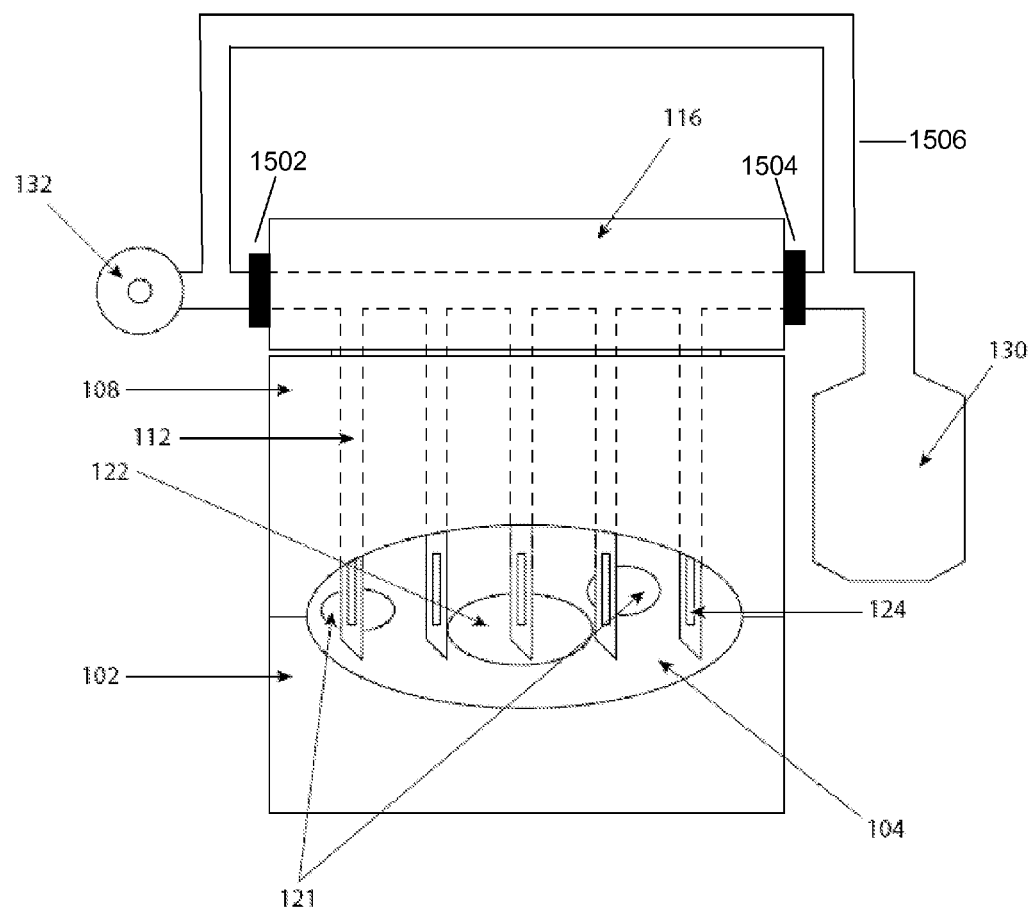
FIG. 15 shows a front view of a device including a shunt and one-way check valves, in accordance with an exemplary embodiment of the present invention.

In one embodiment, after applying the negative pressure to draw blood into a line, a positive pressure may be used to urge fluid in the line into the collection receptacle 130. In this embodiment, the suction and positive pressure may be provided by the withdrawal and depression of the plunger within the barrel of a syringe. To prevent fluid from being expelled via the needles 112, check valves 1406 may be placed in series with each needle 112, as shown in FIG. 14. Alternately, to avoid the need for individual check valves in series with each of the needles, a fluid shunt may be used. As shown in FIG. 15, the shunt 1506 bypasses the device and needles 112 by connecting a first point in the line between the suction source 132 (which, in one embodiment, is a syringe) and the handle 116 to a second point in the line between the collection receptacle 130 and the handle 116. A first check valve 1502 may be placed between the device 100 and the first point in the line. A second check valve 1504 may be placed between the device 100 and the second point in the line. When the plunger of the syringe is withdrawn, a negative pressure is created and fluid should be drawn from the cord 104 and into the line (and may enter the syringe). When the plunger is depressed, fluid is urged through the shunt 1506 and into the collection receptacle 130; the check valves 1502 and 1504 prevent fluid from flowing into the device and out of the needles.

Figure 16:
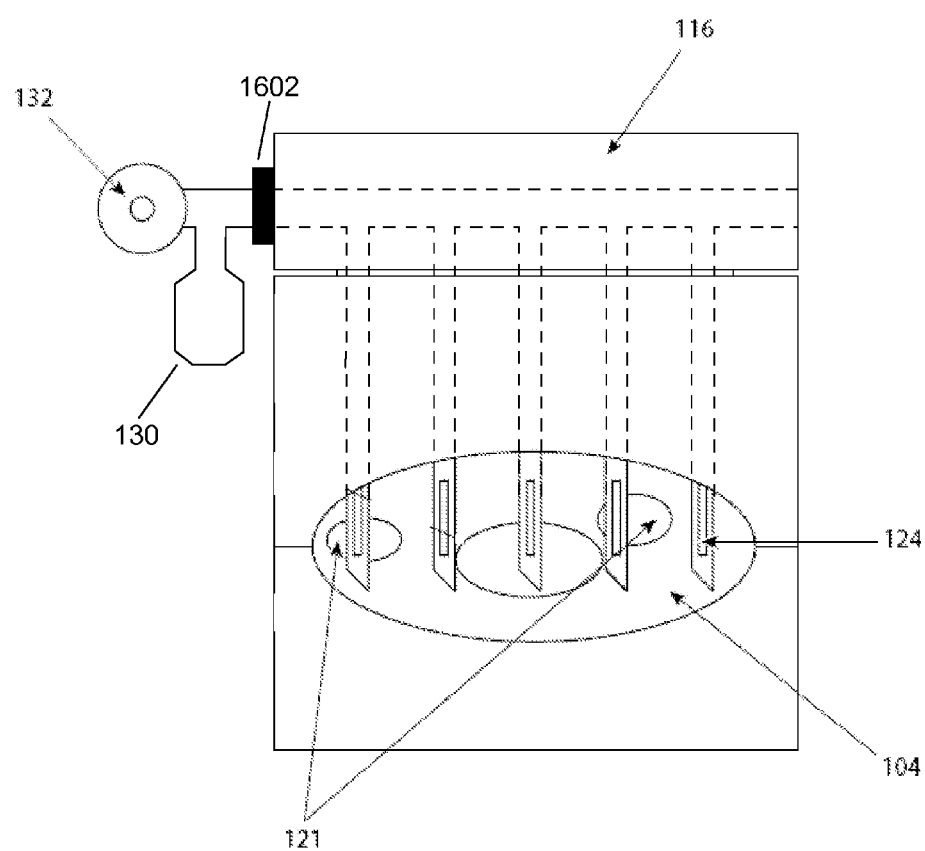
FIG. 16 shows a front view of a device having a conduit, a suction source, a collection bag positioned at an inlet of the conduit, and a one-way check valve between the bag and the device, in accordance with an exemplary embodiment of the present invention.

In another embodiment, the blood collection receptacle may be positioned between the blood collection device and a suction source, as shown in FIG. 16. In this embodiment, a syringe may be used as the suction source 132 and a single check valve 1602 may be used between the bag 130 and the collection device to prevent return of blood to the umbilical cord 104 through the needles 112 when the syringe plunger is depressed. Gravity may be used to urge fluid from the syringe to the collection device 130.

In an alternate embodiment, the suction source is integrated directly into the collection device. For example, a syringe may be attached to the needles 112 via an intervening check valve (not shown). A plunger may be attached to the handle 116 so that withdrawal of the handle 116 causes withdrawal of one or more of the plungers creating a suction to draw fluid into the syringe barrel. Depressing the plunger causes expulsion of the fluid toward the collection receptacle 130 or other receptacle, while the check valve prevents flow of the fluid back into the needles 112 and umbilical cord 104. Alternately, each of the needles may have its own syringe, plunger and check valve.

Methods to Increase Blood Flow from the Placenta to the Umbilical Cord

Collection, in some embodiments, is accomplished without compressing the cord and completed before placental separation has occurred. In one embodiment of the method, as show in FIG. 9, a bag 133 or other constricting device is placed over the placenta 135 and the bag is closed using a reclosable bag sealing mechanism 139, which, in one embodiment, is a zipper-strip bag actuated by a slider, but in other embodiments is any mechanism for sealing a bag. In some embodiments, the bag is leak-proof. A suction force is connected via tubing to a port located at a pocket of the bag 133 and used to remove air from the bag 133. Removal of air results in sub-ambient pressure around the placenta 135. The pressure differential between the ambient air pressure (about 1 bar) and the sub-ambient pressure within the bag 133, will urge blood to flow to the umbilical cord 104. Depressurization of the placenta 135 in some embodiment can improve the yield of blood when blood is collected from the umbilical cord 104.

Figure 9:
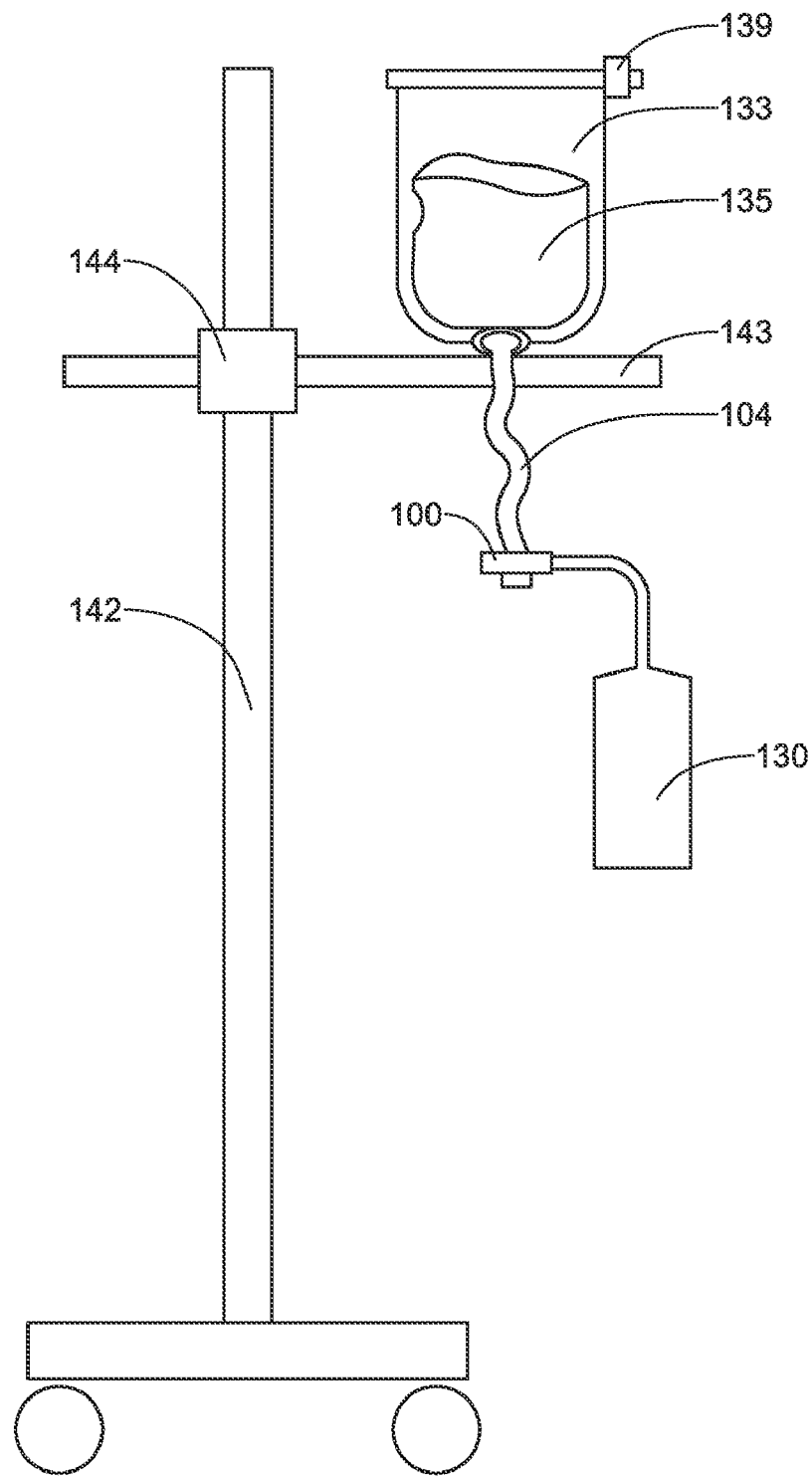
FIG. 9 shows a system for extracting stem cells from an umbilical cord and placenta in accordance with an exemplary embodiment of the present invention.

As shown in FIG. 9, an adjustable clamp 144 on a vertical pole 142 can be used in some embodiments to support a placenta 135 in an elevated position relative to the umbilical cord 104 so that gravity will urge blood to flow from the placenta 135 to the umbilical cord 104. In some embodiments, the adjustable clamp 144 is a ring clamp balanced with a counter weight. In this embodiment the placenta 135 is placed on a carrier plate 143 and the umbilical cord 104 hangs below the placenta. Gravity forces blood from the placenta 135 to the umbilical cord 104, through the collection device 100 and into the blood collection receptacle 130. In other embodiments, the adjustable clamp 144 can be any mechanism capable of functioning to allow for adjustment around a pole 142.

Blood Collection and Stem Cell Separation Procedures

In the embodiment shown in FIG. 9, blood is collected from the collection device 100 into the collection receptacle 130. In accordance with the embodiment, the umbilical cord blood is mixed with an anticoagulant immediately upon collection. The anticoagulant may be any anticoagulant known in the art, including but not limited to CPD (citrate-phosphate-dextrose), ACD (acid citrate-dextrose), Alsever's solution (Alsever, J. B. and Ainslie, R. B., 1941, N.Y. St. J. Med. 41:126), De Gowin's Solution (De Gowin, E. L., et al., 1940, J. Am. Med. Ass. 114:850), Edglugate-Mg (Smitt, W. W., et al., 1959, J. Thorac. Cardiovasc. Surg. 38:573), Rous-Turner Solution (Rous, P. and Turner, J. R., 1916, J. Exp. Med. 23:219), other glucose mixtures, heparin, and ethyl biscoumacetate. In the preferred embodiment ACD can be used.

After receiving umbilical cord blood and mixing with an anticoagulant such as acid citrate dextrose (ACD), the blood can be subjected to physical and/or immunological cell separation procedures. Such procedures separate the umbilical cord stem cells so that fewer total cells have to be stored and transplanted. Various procedures are known in the art and can be used to separate the umbilical cord stem cells and other useful progenitor cells. These include but are not limited to equilibrium density centrifugation, velocity sedimentation at unit gravity, immune resetting and immune adherence, counter-flow centrifugal elutriation, T lymphocyte depletion, and fluorescence-activated cell sorting, alone or in combination. In one embodiment of the method, collected blood is centrifuged and the plasma is removed for isolation of stem cells and other progenitor cells. Recently, procedures have been reported for the isolation of very highly enriched populations of stem cells. In some procedures, it has been found that the existence of red blood cells is beneficial to the viability of the stem cells, which may be considered in separation procedures.

As an example of a separation procedure, umbilical cord stem cells are present in the non-adherent, low density, T-lymphocyte-depleted fraction of cord blood cells. In a specific embodiment, low density cells can be separated by use of Ficoll-Hypaque (Pharmacia Fine Chemicals, Piscataway, N.J.) or Percol (Broxmeyer, H. E., 1982, J. Clin. Invest. 69:6320642). In this procedure, the mature cells of the granulocytic series, which are not needed for transplantation, are removed in the dense fraction that goes to the bottom of the tube. An adherence/nonadherence separation protocol can also be used for enrichment of umbilical cord stem cells, protocols that are described in Section 6/3/2, infra, and in Broxmeyer, H. E., et al 1984, J. Clin. Invest. 73:939-953.

In accordance with some embodiments of the methods and device described, stem cells are enriched from umbilical cord blood. In order to enrich umbilical cord stem cells, in one embodiment, cell separation procedures that entail immunological recognition of cells are used. Umbilical cord stem cells can be isolated from blood by positive or negative selection using antibodies that recognize antigenic determinants on the surface of cells. In one embodiment, separation of the cells can be achieved by the use of monoclonal antibodies that recognize cell surface determinants on these cells, in conjunction with separation procedures such as fluorescence-activated cell sorting or panning (Broxmeyer, H. E., et al., 1984, J. Clin. Invest. 73:939-953). While specific antigenic determinants may not be known for umbilical cord stem cells, the stem cells do contain antigenic determinants that are not present on all other cells, which can be used in antibody selection protocols for enrichment purposes.

Several antigenic determinants have been isolated as unique to stem cells. In specific embodiments, antibodies with are currently available and can be used in enrichment protocols include My-10, 3C5, or RFB-1. These antibodies can be used alone or in combination with procedures such as spanning (Broxmeyer, H. E., et al., 1983, J. Clin. Invest. 73:939-953) or fluorescence activated cell-sorting (FACS) (Williams, D. E., et al., 1985, J. Immunol. 135:1004; Lu, L., et al., 1986, Blood 68(1): 126-133) to isolate those cells containing surface determinants recognized by the monoclonal antibodies.

Other methods of enrichment of umbilical cord stem cells include the use of monoclonal antibodies to major histocompatibility (MHC) class II antigens (especially HLA-DR) and to MY10 (Lu, L., et al., 1987, J. Immunol. 139(6): 1823-1829. In another method T lymphocyte depletion can be used to enrich for umbilical cord stem cells. In this procedure, T lymphocytes are selectively removed from the cell population by pretreating cells with a monoclonal antibody that recognizes a T cell antigen, plus complement. Such a procedure has been described previously (Broxmeyer, H. E., et al., 1984, J. Clin, Invest. 73:939-953). In yet another method, umbilical cord stem cells can be separated and removed from blood by selective agglutination using a lectin such as soybean (Reisner, Y., et al., 1980, Proc. Natl. Acad. Sci. U.S.A. 77:1164). This procedure can be a viable alternative for separation and enrichment of umbilical cord stem cells without removal of possibly necessary accessory cells (Reisner, Y., et al., 1983, Blood 61(2):341-348; Reisner, Y., et al., 1982, Blood 59(2): 360-363).

Freezing of Stem Cells and Cryoprotective Agents

Freezing is an important step of preservation of umbilical cord stem cells and other progenitor cells in accordance with various embodiments of the method. The freezing of cells is ordinarily destructive because water within the stem cells freezes. Injury then often occurs by osmotic effects on the cell membrane, cell dehydration, solute concentration, and ice crystal formation. As ice forms outside the cell, available water is removed from solution and withdrawn from the cell, causing osmotic dehydration and raised solute concentration that eventually destroy the cell. (Mazur, P., 1977, Cryobiology 14:251-272.)

The injurious effects of freezing cells can be circumvented by a number of ways, including but not limited to: (a) use of cryoprotective agents, (b) control of the freezing rate, and (c) storage at a temperature sufficiently low to minimize degradative reactions. Cyroprotective agents that can be used to protect umbilical cord stem cells in accordance with the present invention include but are not limited to dimethyl sulfoxide (DMSO) (Lovelock, J. E. Ashwood and Bishop, M. W. H. 1959, Nature 183:1394-1395; Ashwood-Smith, M. J., 1961, Nature 190:1214-1215. In a preferred embodiment in accordance with the method, DMSO is used, a liquid small molecule, DMSO freely permeates the cell and protects intracellular organelles by combining with water to modify its freezability and prevent damage from ice formation. Addition of plasma (e.g. to a concentration of 20-25%) can also augment the protective effects of DMSO. After addition of DMSO, cells should be kept at 0° C. until freezing, since DMSO concentrations of about 1% are toxic at temperatures above 4° C.

A controlled slow cooling rate is very important because different cell types have different cooling rates (see e.g. Rowe, A. W. and Rinfret, A. P., 1962, Blood 20:636; Rowe, A. W., 1966, Cryobiology 3(1):12-18: Lewis, J. P., et al., 1967, Transfusion 7(1):17-32; and Mazur, P., 1970, Science 168: 9393-949 or effects of cooling velocity on survival or marrow-stem cells and on their transplantation potential). Known methods of cooling stem cells for administration to a patient include but are not limited to a programmable freezing device or a methanol bath procedure. Programmable freezing apparatuses allow determination of optimal cooling rates and facilitate standard reproducible cooling. Programmable controlled-rate freezers such a Cryomed or Planar permit tuning of the freezing regimen to the desired cooling rate curve. Generally, the container holding the cells in a programmable freezing apparatus must be stable at cryogenic temperatures and allow for rapid heat transfer for effective control of both freezing and thawing. Sealed plastic vials (e.g., Nunc, Wheaton cryules) or glass ampules can be used for multiple small amounts (1-2 ml), while larger volumes (100-200 mls) can be frozen in polyolefin bags (e.g., Delmed) held between metal plates for better heat transfer during cooling.

In an alternative known cooling method for umbilical cord blood stem cells, a methanol bath may be used. The methanol bath method is well suited for routine cryopreservation of multiple small items on a large scale. The method does not require manual control of the freezing rate nor a recorder to monitor the rate. In a preferred method, DMSO-treated cells are precooled on ice and transferred to a tray containing chilled methanol which is placed in turn in a mechanical refrigerator (e.g., Harris or Revco) at −80° C.

After thorough freezing, cells can be rapidly transferred to a long-term cryogenic storage vessel. In a preferred embodiment, samples can by cryogenically stored in liquid nitrogen (−196° C.) or its vapor (−165° C.). Such storage is greatly facilitated by the availability of highly efficient liquid nitrogen refrigerators, which resemble large thermos containers with an extremely low vacuum and internal super insulation, such that heat leakage and nitrogen losses are kept to an absolute minimum.

Thawing of Stem Cells

Thawing of stem cells is a very delicate process that requires caution in order to maintain the viability of the cells and their therapeutic benefit. Immediate delivery of stem cells upon thawing from a frozen state improves the viability of the stem cells. Embodiments of the method include a method of gently thawing frozen stem cells and delivering them quickly to a patient in order to maintain cell viability and therapeutic benefit. A source of frozen stem cells and a cell-delivery fluid are provided. The cell-delivery fluid is then transported to the frozen stem cells to thaw the cells so that they mix with the cell-delivery fluid and the mixture is transported to the patient. The cell-delivery fluid can be any fluid or mixture of fluids compatible with stem cells and suitable for intravenous administration to a patient and may be a fluid derived from blood including whole blood, serum or blood plasma or may be a IV fluid such as normal saline or lactated Ringer's solution. The cell-delivery fluid could also be a mixture of an IV fluid and a fluid derived from blood. The cell-delivery solution could include a synthetic substance such as a perfluorocarbon. Perfluorocarbons known to be safe for intravenous delivery include perfluorodecalin and perfluorooctane. The cell-delivery fluid may advantageously be warmed before contacting it with the stem cells.

Figure 10:
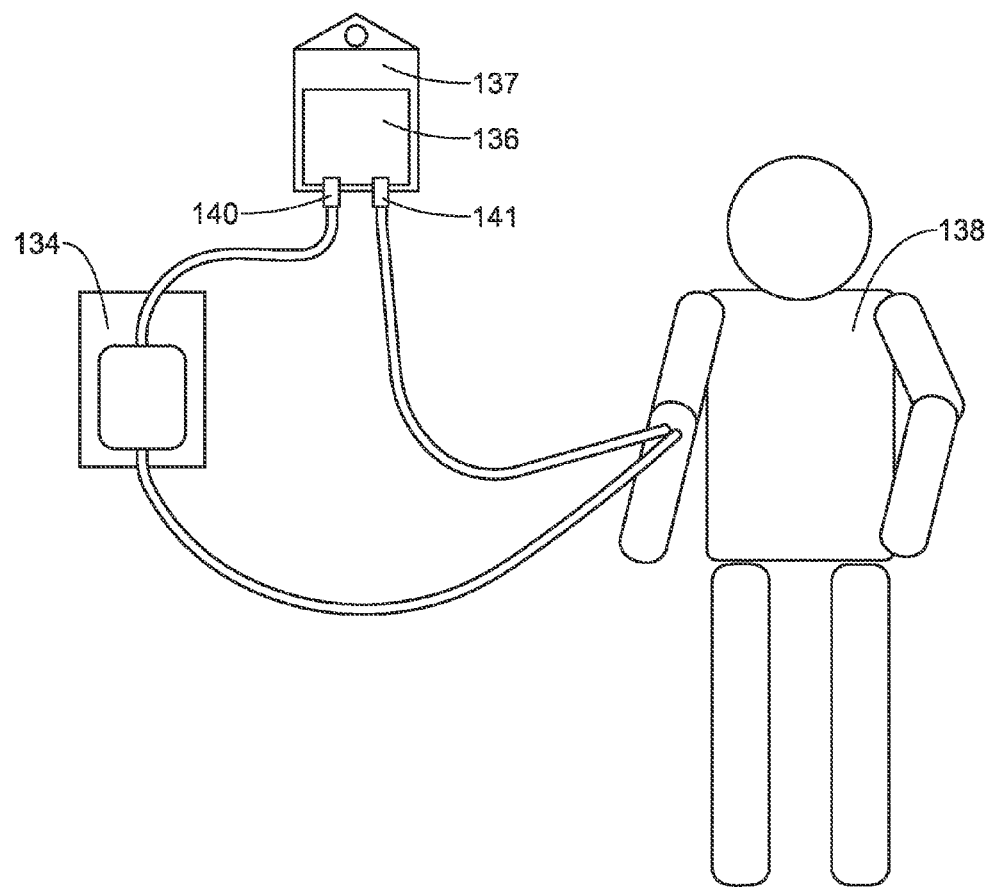
FIG. 10 shows a system for delivering stem cells to a patient in accordance with an exemplary embodiment of the present invention.

If a fluid derived from blood is used, it may be derived from the blood of the patient to be treated to avoid transfusion. FIG. 10 shows one embodiment of a system for thawing frozen stem cells held in a delivery bag 137. The frozen cells 136 are preferably thawed quickly and administered to a patient 138 immediately upon thawing. A pump may be used to transport blood from a patient 138 through a warming device 134 and into a delivery bag 137 via an inlet 140. The so warmed blood thaws the frozen stem cells 136 and the blood. The thawed stem cells are then pumped back to the patient 138 though an outlet 141. Blood may be taken continuously or intermittently from a patient 138 and continuously or intermittently contacted with the frozen stem cells 136 to thaw the cells and then continuously or intermittently returned to the patient 138.

In alternate embodiment of the system described with respect to FIG. 10, blood can be pumped immediately from the patient 138 to thaw the frozen stem cells 136, without passing through a warming device. The thawed stem cells are then pumped back to the patient 138 through the outlet 141. The blood and thawed stem cell mixture may be warmed before return to the patient 138.

In other embodiments, an IV fluid can be warmed and pumped into the frozen stem cells 136 and then immediately delivered to patient 138 upon thawing of stem cells. Alternately, an IV fluid and a patient's blood can be mixed, warmed and pumped into frozen stem cells 136 and delivered to patient 138 immediately upon thawing of the stem cells. The IV fluid and blood may be warmed before or after mixing.

Figure 11:
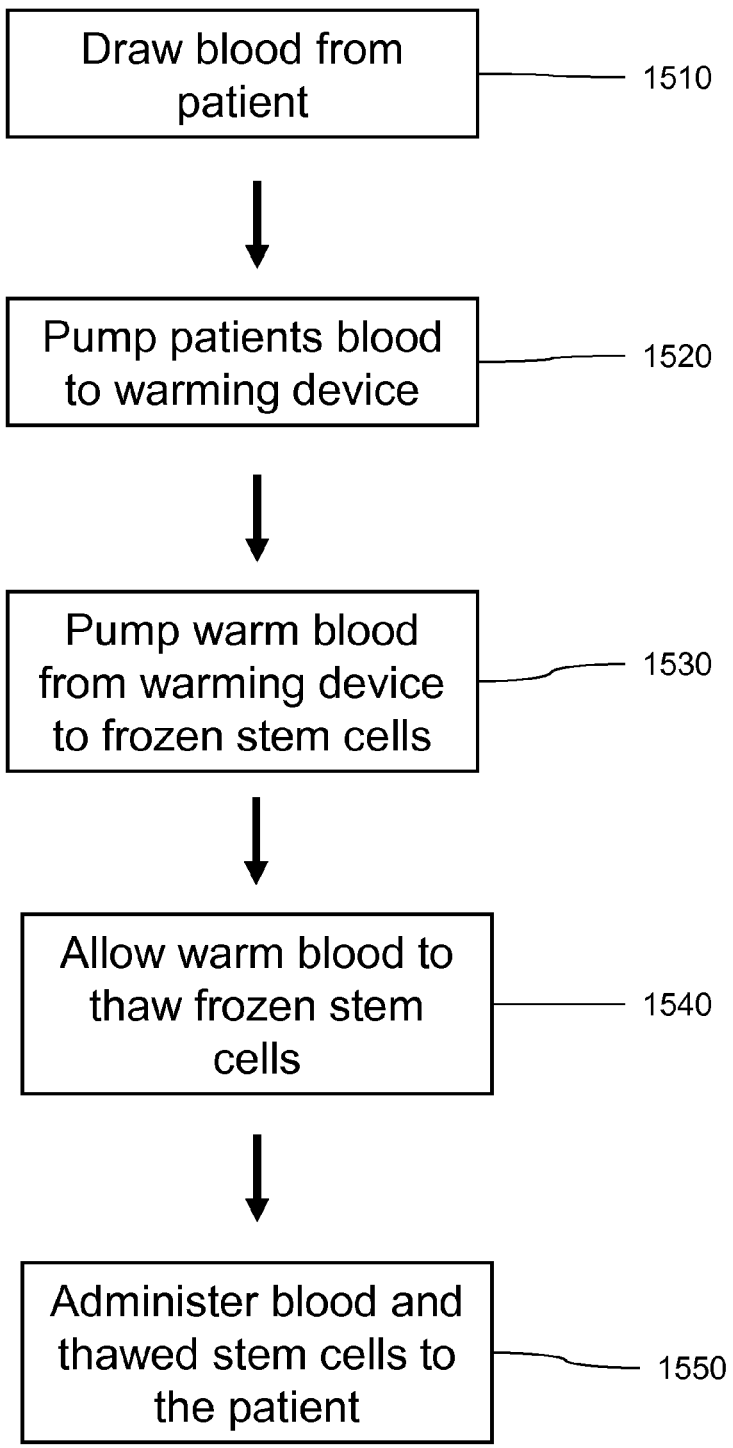
FIG. 11 shows a flow chart of a method for thawing and delivering stem cells to a patient using warmed blood in accordance with an exemplary embodiment of the present invention.

FIG. 11 shows a flow chart for one embodiment of a method for thawing frozen stem cells using a patient's blood and delivering the thawed stem cells to a patient. First, blood is drawn from a patient, typically through a needle inserted into a vein of the patient (step 1510). The patient's blood is then pumped to a warming device and the blood is warmed (step 1520). The warm blood is then pumped to the frozen stem cells (step 1530). A sufficient time or flow rate is used to allow the frozen stem cells to thaw while in contact with the warm blood (step 1540). The thawed stem cells are then administered to the patient (step 1550).

Figure 12:
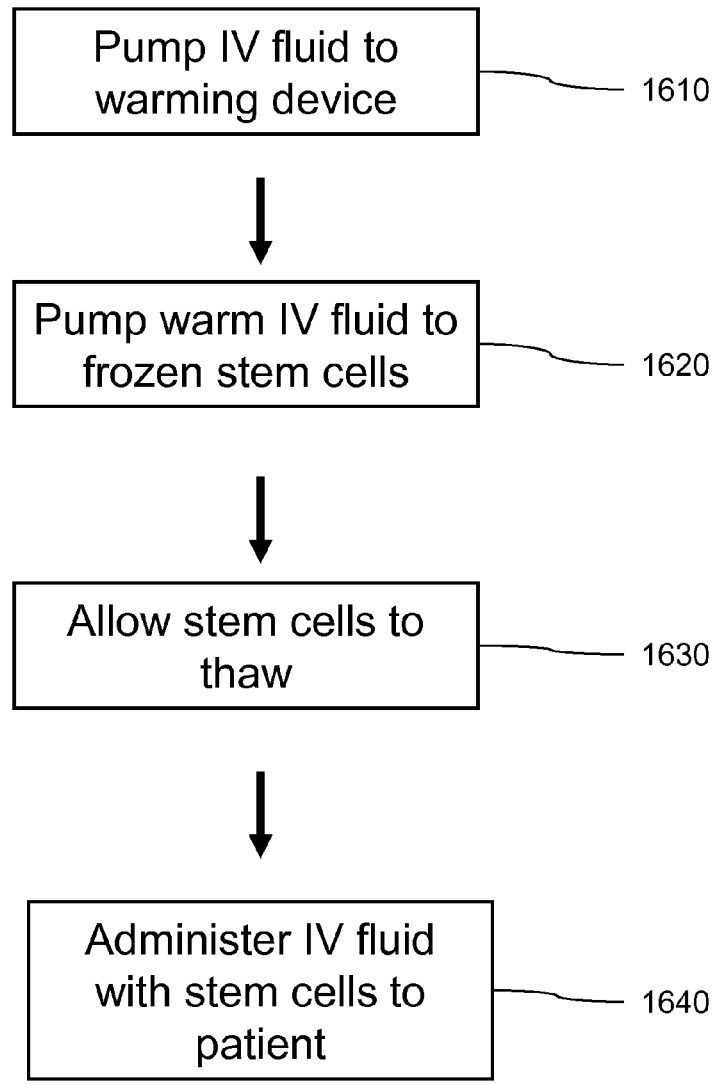
FIG. 12 shows a flow chart of a method for thawing and delivering stem cells to a patient using warmed IV fluid in accordance with an exemplary embodiment of the present invention.

FIG. 12 shows a flow chart for one embodiment of a method for thawing frozen stem cells using an IV fluid such as normal saline or Ringer's solution and delivering the thawed stem cells to a patient. First, IV fluid is pumped from a source reservoir to a warming device and warmed (step 1610). The warm IV fluid is then pumped to the frozen stem cells (step 1620). A sufficient contact-time or flow rate is used to allow the frozen stem cells to thaw while in contact with the IV fluid (step 1630). The thawed stem cells are then administered to the patient (step 1640).

Figure 13:
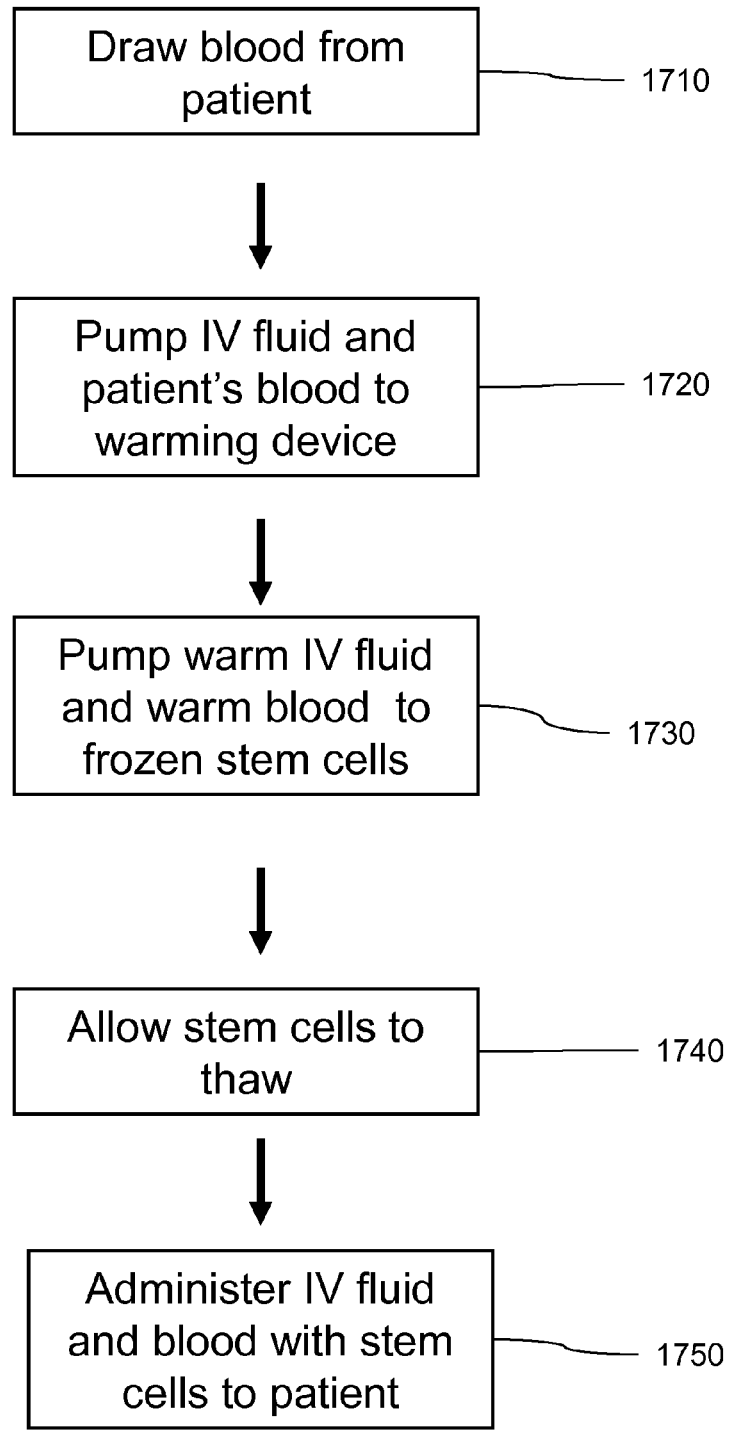
FIG. 13 shows a flow chart of a method for thawing and delivering stem cells to a patient using both warmed blood and warmed IV fluid in accordance with an exemplary embodiment of the present invention.

FIG. 13 shows one embodiment of a method for thawing frozen stem cells using a mixture of a patient's blood and an IV fluid such as normal saline or Ringer's solution and delivering the thawed stem cells to a patient. First, blood is drawn from the patient (step 1710). The blood is mixed with an IV fluid and pumped to a warming device and allowed to warm (step 1720). The blood and warm IV fluid mixture is then pumped to the frozen stem cells (step 1730). A sufficient contact-time or flow rate is used to allow the frozen stem cells to thaw while in contact with the blood and IV fluid mixture (step 1740). The thawed stem cells are then administered to the patient (step 1750).

The following methods of thawing stem cells may be used in accordance with the various embodiments of the method described. This method includes immersing frozen stem cells in a vial containing the frozen stem cells up to the neck of the vial in a warm water bath. Gentle rotation of the vial will ensure mixing of the cell suspensions as it thaws and increase heat transfer from the warm water to the internal ice mass. As soon as the ice has completely melted in accordance with this method, the vial can be immediately placed on ice.

In some embodiments, it may be desirable to treat the cells in order to prevent cellular clumping upon thawing. To prevent clumping, various procedures can be used, including but not limited to, the addition of DNase before and/or after freezing (Spitzer, G., et al., 1980, Cancer 45:3075-3085.

The cryoprotective agent, if toxic in humans, should be removed prior to therapeutic use of the thawed umbilical cord stem cells. In an embodiment employing DMSO as the cryopreservative, it is preferable to omit this removal step in order to avoid cell loss, since DMSO has no serious toxicity to humans. However, where removal of the cryoprotective agent is desired, the removal is preferably accomplished upon thawing.

One way to remove the cryoprotective agent is by dilution to an insignificant concentration. This can be accomplished by addition of a medium, followed by, if necessary, one or more cycles or centrifugation to pellet cells, removal of the supernatant, and re-suspension of the cells.

After removal of the cryoprotective agent, cell count (e.g. by use of hemocytometer) and viablility testing (e.g., by trypan blue exclusion) can be done to confirm cell survival (Kuchler, R. J. 1977, Biochemical Methods in Cell culture and Virology, Dowden, Hutchinson & Ross, Strousburg, Pa., pp. 18-19; 1964, Methods in Medical Research, Eisen, H. N. et al., eds., Vol 10, Year Book Medical Publishers, Inc., Chicago, pp 39-47).

Other procedures that can be used, relating to processing of the thawed cells, include enrichment of umbilical cord stem cells by in vitro culture. However these steps can be omitted in order to minimize cell loss.

Thawed cells may be tested by standard assays of viability (Med, trypan blue exclusion) of microbial sterility and tested to confirm and/or determine their identity relative to the patient and for umbilical cord stem cell function.

While the principles of the invention have been described herein, it is to be understood by those skilled in the art that this description is made only by way of example and not as a limitation as to the spirit and scope of the invention. Other embodiments are contemplated within the scope of the present invention in addition to the exemplary embodiments shown and described herein. Modifications and substitutions by one of ordinary skill in the art are considered to be within the scope of the present invention. Various references are cited herein, the disclosures of which are incorporated by reference in their entireties.

What is claimed is:

1. An umbilical cord collection device for collecting fluid comprising:
a needle carrier comprising a plurality of receiving holes for receiving a plurality of needles wherein the needles are inserted into the receiving holes and extend from the needle carrier, and wherein the needles are provided in parallel arrangement with one another in the needle carrier;
a holder comprising a chamber whereby the holder clamps the umbilical cord into the chamber, the holder comprising an upper portion comprising a guide opening, wherein the guide opening receives the plurality of needles; and
a backstop, wherein the upper portion is hingably attached to the backstop, the upper portion having an open position and a closed position, wherein the chamber is formed between the upper portion and the backstop, and wherein when the upper portion is in the closed position the chamber holds the umbilical cord; and
a handle attached to the needle carrier and having a size larger than the guide opening, the handle for applying force to the needle carrier so as to simultaneously force the plurality of needles through the guide opening into the chamber and into the umbilical cord held in the chamber, whereby fluid communication between a source of blood in the umbilical cord and the plurality of needles is formed.

2. The device according to claim 1 wherein the needle carrier is slidably mounted with respect to the guide opening.

3. The device according to claim 1 wherein more than one of the plurality of needles have an output into a common conduit.

4. The device according to claim 3 wherein the conduit is integral to the needle carrier.

5. The device according to claim 3 further comprising a collection bag in fluid communication with the conduit.

6. The device according to claim 5 further comprising a source of suction in communication with the conduit.

7. The device according to claim 6 further comprising a one-way check valve located between the conduit and the source of suction.

8. The device according to claim 5 wherein the collection bag contains an anticoagulant.

9. The device according to claim 1 further comprising a sealable bag for encasing a placenta.

10. The device according to claim 9 wherein the bag has a port for attaching a source of suction.

11. The device according to claim 10 wherein the source of suction is selected from the group consisting of a pump and a syringe.

12. The device according to claim 1 wherein the chamber has a height less than the diameter of the cord so as to flatten the umbilical cord.

13. The device according to claim 1 wherein the chamber interior has a rough structure for gripping the cord.

14. The device according to claim 1 wherein the backstop is resistant to puncture.

15. The device according to claim 1 further comprising fenestrated needles attached to the needle carrier.

* * * * *